United States Patent

Vanlerberghe et al.

[11] 4,138,427
[45] Feb. 6, 1979

[54] SEQUENCED SURFACTANT OLIGOMERS OF THE POLYHYDROXYLATED POLYETHER TYPE, PROCESS FOR PREPARING THEM AND COMPOSITION CONTAINING THEM

[75] Inventors: Guy Vanlerberghe, Claye-Souilly; Henri Sebag, Paris, both of France

[73] Assignee: L'Oreal, France

[21] Appl. No.: 815,848

[22] Filed: Jul. 14, 1977

[30] Foreign Application Priority Data

Jul. 16, 1976 [LU] Luxembourg ............... 75405

[51] Int. Cl.$^2$ ............... C07C 87/20; C07C 87/30; C07C 140/00; A61K 31/14
[52] U.S. Cl. ............... 260/459 A; 252/547; 252/DIG. 13; 260/456 R; 260/456 P; 260/501.13; 260/501.17; 260/567.6 P; 260/584 B; 260/607 AL; 260/609 R; 424/70; 568/614; 568/624
[58] Field of Search ....... 260/501.13, 584 B, 607 AL, 260/609 R, 567.6 P, 456 R, 456 P, 459 A, 501.17

[56] References Cited

U.S. PATENT DOCUMENTS

| | | | |
|---|---|---|---|
| 3,428,680 | 2/1969 | Walker et al. | 260/567.6 P |
| 3,454,646 | 7/1969 | Patton et al. | 260/584 B |
| 3,906,048 | 9/1975 | Vanlerberghe et al. | 260/609 R |
| 3,912,662 | 10/1975 | Martinsson et al. | 260/501.13 |

*Primary Examiner*—Joseph E. Evans
*Attorney, Agent, or Firm*—Cushman, Darby & Cushman

[57] ABSTRACT

Polyhydroxylated sequenced oligomer surfactants of the formula:

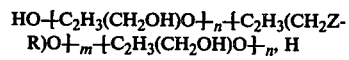

where R is $C_{14}$-$C_{18}$ alkyl, Z represents $NR_1$, $HN^{30}R_1V^-$, $R_1N\rightarrow O$, $R_1NO^+HV^-$, $R_1N^+CH_2COO^-$, $R_1R_2N^+Y^-$, $R_1R_2NX^-$ or $S\rightarrow(O)a$ wherein $R_1$ and $R_2$ are methyl, ethyl or hydroxyethyl; X is Cl or Br, Y is an anion and V is an anion. The oligomers are prepared by successively telomerizing on tertiobutyl alcohol, tertiobutyl glycidyl ether, then epihalohydrin. The tertiobutoxy and halogen substituents are then replaced by OH and Z groups respectively. These compounds can be used as surfactants in, particularly, cosmetic compositions.

10 Claims, No Drawings

SEQUENCED SURFACTANT OLIGOMERS OF THE POLYHYDROXYLATED POLYETHER TYPE, PROCESS FOR PREPARING THEM AND COMPOSITION CONTAINING THEM

The present invention relates to new sequenced oligomer surfactants of the polyhydroxylated polyether type; to a process for their preparation; to their use; and to polyhalogenated polytertiobutoxy intermediates as well as polyhalogenated polyhydroxylated intermediates.

A significant number of surface active agents are presently known whose structure exhibits a lipophilic chain and a hydrophilic chain, wherein the lipophilic chain is constituted by a fatty aliphatic or aryl-aliphatic hydrocarbon chain having from 8 to 18 carbon atoms. These products have found numerous uses in the most varied fields. They exhibit a variety of structures although it has been found that their properties are limited by the nature of the lipophilic portion thereof.

In order to overcome this disadvantage, it has been proposed to replace the hydrocarbon chain of conventional surfactants by a lipophilic sequence obtained from the polymerization of an alkylene oxide having at least three carbon atoms.

This concept has been disclosed in U.S. Pat. No. 2,677,700 and in accordance with a preferred embodiment of the invention disclosed therein, the lipophilic sequence is a polyoxypropylene chain and the hydrophilic sequence is a polyoxyethylene chain.

According to U.S. Pat. No. 3,454,646, the polyoxyethylene chain is replaced by a sequence selected from (dialkyl amino-methyl)-ethyleneoxy or (N-oxydialkyl amino-methyl)-ethyleneoxy; the lipophilic sequence being obtained by the reaction of a lower alkylene oxide with a monoalcohol or a polyol.

It is also generally known that the surface activity of an amphiphile compound increases with the length of the lipophile chain. The works of T. Kuwanura (Kobunshi Kagaku 17, pp. 175–182, 1960) have shown that in the case of polymer sequences produced from alkyl glycidyl ethers and ethylene oxide, this rule is confirmed.

However, until now, it has not been possible to obtain sequence structured polyethers having, simultaneously high surface activity and satisfactory water-solubility characteristics.

The present invention provides products which possess in combination the following advantageous properties: surface activity, affinity for water, chemical stability and weak mucous aggressiveness.

Thus, the present invention relates to bisequenced and trisequenced oligomer surfactants of the formulas A-B and A-B-A', respectively. These surfactants can be represented by the general formula:

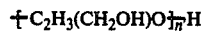

wherein
R represents linear alkyl having 4–18 carbon atoms and having, preferably an even number of carbon atoms;

Z represents a member selected from

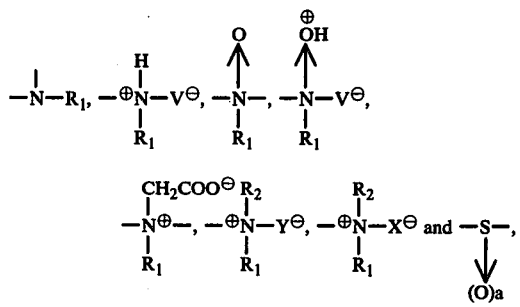

wherein $R_1$ and $R_2$ each independently represent methyl, ethyl or hydroxyethyl;

$X^\ominus$ represents $Cl^\ominus$ or $Br^\ominus$;

$y^\ominus$ represents an anion and, preferably chloride, bromide, iodide, methyl sulfate, methane sulfonate or paratoluene sulfonate;

$HR_1N^+V^-$ and $R_1NO^+HV^-$ represent mineral or organic salts of an amine or amine oxide, and preferably a hydrochloride, hydrobromide, sulfate, phosphate, acetate, lactate, tartrate, oxalate or succinate;

a represents 0 or 1;

$+C_2H_3(CH_2OH)O+$ represents the two isomers;

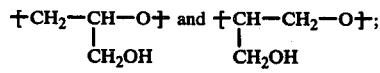

$+C_2H_3(CH_2ZR)O+$ represents the two isomers;

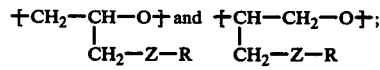

m represents a whole or decimal number from 2 to 10;
n represents a whole or decimal number from 2 to 25;
n' represents 0 or a whole or decimal number from 2 to 25; and
the sum n + n' represents a whole or decimal number from 2 to 25.

The values m, n and n' are numbers corresponding to statistical averages and represent the degrees of polymerization; the actual number of units for each sequence in a given compound being lower or higher than the statistical average.

The present invention also relates to a three stage process for preparing the bisequenced compounds of formula (I) of the type, A-B (n' = 0) and the trisequenced compounds of the type A-B-A' (n' ≠ 0 and n + n' = 2-25).

In the preparation of a bisequenced oligomer surfactant, this process comprises the following steps:

(1) In a first stage an intermediate oligomer is prepared by the telomerization of tertio-butyl glycidyl ether on a tertio-butyl alcohol followed by the telomerization of an epihalohydrin such as epichlorhydrin or epibromhydrin on the previously obtained telomer, which serves as the telogen, according to the following reactions:

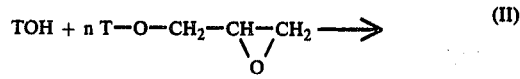

-continued $$T-O\{C_2H_3(CH_2OT)O\}_{\overline{n}}H$$

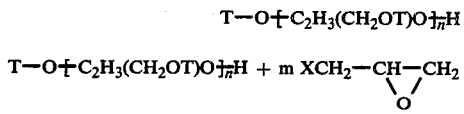

$$T-O\{C_2H_3(CH_2OT)O\}_{\overline{n}}\{C_2H_3(CH_2X)O\}_{\overline{m}}H$$

In these reactions T represents the tertiobutyl group,

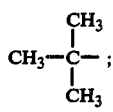

X represents Cl or Br; the unit $-\!\!+\!C_2H_3(CH_2OT)O\!+\!\!-$ represents the two isomers:

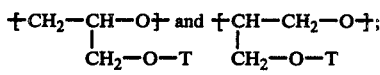

and the unit $-\!\!+\!C_2H_3(CH_2X)O\!+\!\!-$ represents the two isomers:

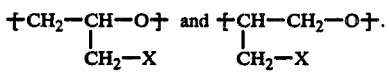

In the preparation of a trisequenced oligomer surfactant, the intermediate compound of formula (II), is telomerized with n' moles of tertiobutyl glycidyl ether according to the reaction:

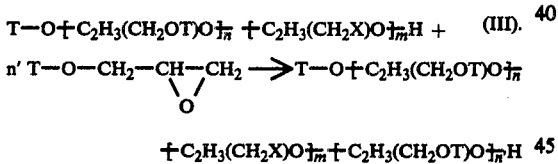

$$-\!\!+\!C_2H_3(CH_2X)O\!+\!\!_{\overline{m}}\!-\!\!+\!C_2H_3(CH_2OT)O\!+\!\!_{\overline{n}}\!H \quad (III).$$

These telomerization reactions are carried out at a temperature from 50 to 110° C. and preferably from 60 to 80° C., in the presence of a Lewis acid catalyst, and preferably in the presence of boron trifluoride, tin tetrachloride or antimony pentachloride.

The weight amount of catalyst relative to the reaction mass is from 0.1–3 percent, and preferably from 0.2 to 1.5%.

The catalyst is introduced preferably in fractions to avoid having too high a concentration thereof at the beginning of the polymerization reaction.

Generally, the catalyst and the epoxide group containing compound for each of the sequences being prepared are added alternately in portions (from one to four).

After the telomerization reaction, the reaction mass is washed with water, in the presence of a sufficient amount of basic compound which is preferably, sodium hydroxide, to neutralize the catalyst. After drying under reduced pressure, the volatile compounds are generally removed by molecular distillation.

The molecular weight of the intermediate compounds is between 500 and 5,000 and generally between 800 and 3,000.

(2) In a second stage the tertiobutoxy groups, (OT), are replaced by OH groups in the presence of an acid catalyst and preferably in the presence of a sulfocarboxylic acid at a temperature of 80–110° C. for 1–4 hours. The replacement of the tertiobutoxy groups by OH groups is described more fully in French Pat. No. 2,027,585 and U.S. Pat. No. 3,840,606, incorporated herein by reference.

(3) In a third stage the halogen substituent X is replaced by a group selected from:

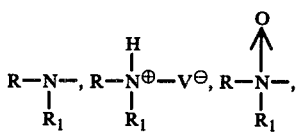

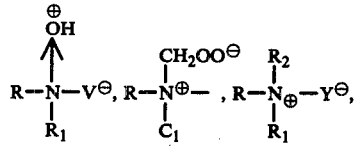

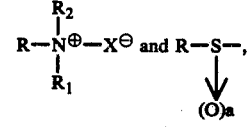

wherein R, $R_1$, $R_2$, $X^\ominus$, $Y^\ominus$, $RR_1N^\oplus HV^\ominus$, $RR_1NO^\oplus HV^\ominus$ and a have the meanings given above. Step 3 can be accomplished in the following alternative ways:

(3a) by reaction of the halogenated telomer with a secondary amine, optionally followed by oxidation and/or salification or betainization; or (3b) by reaction of the halogenated telomer with a tertiary amine; or (3c) by reaction of the halogenated telomer with an alkaline alkyl mercaptide and preferably with a sodium or potassium alkyl mercaptide; it being understood that the order of stages 2 and 3 can be reversed.

The replacement of the halogen atoms of the polyhalogenated polytertiobutyl intermediate compounds of formulas (II) or (III) obtained in the first stage, or of the polyhalogenated polyhydroxylated intermediate compounds obtained in the second stage, by

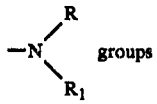

is effected by the reaction of said intermediate compounds with a secondary amine of the formula

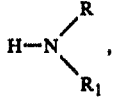

wherein R and $R_1$ have the meanings given above, at a temperature of 80–180° C. without a solvent or in the presence of a solvent for at least one of the reactants which solvent, advantageously, is selected from alcohols, ethers and alkoxy alkanols and preferably, ethanol, ethyleneglycol, diethyleneglycol, dipropyleneglycol, the monomethyl-, monoethyl- or monobutyl-ethers of either monoethylene glycol or diethylene glycol.

Preferably an excess of at least 100% of the secondary amine to neutralize the hydracid formed is employed.

As the secondary amine there is used, preferably, N-methyl or N-ethyl alkylamines. The alkyl group has from 4–18 carbon atoms and is selected from, preferably, butyl, hexyl, octyl, decyl, dodecyl, tetradecyl, hexadecyl or octadecyl.

This reaction with the secondary amine can be followed by oxidation of the polyamine obtained to a corresponding polyamine oxide by means of an appropriate oxidizing agent which is, advantageously, H₂O₂, preferably at a concentration of about 39 weight percent. Other oxidizing agents can also be used such as a peracid, including performic or peracetic acid. The reaction with the secondary amine can also be followed by a salification reaction using a mineral acid such as hydrochloric, hydrobromic, sulfuric and phosphoric acids, or an organic acid such as acetic, lactic, tartaric, oxalic or succinic acids.

The replacement of the halogen atoms of the intermediate compounds obtained in the first stage or in the second stage by a

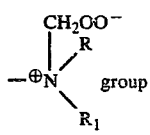

is carried out initially by the reaction with a secondary amine of the formula

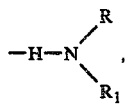

as indicated above, followed by a betainization reaction using an alkaline monochloroacetate, which is preferably sodium or potassium monochloroacetate.

The replacement of the halogen atoms of the intermediate compounds by a

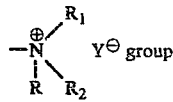

is carried out by initially reacting it with a secondary amine of the formula

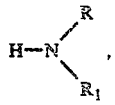

as indicated above, and then by quaternizing the polytertiobutoxy polyamine or polyhydroxylated polyamine with a quaternizing agent or a classic alkylating agent, for example, with a methyl- or ethyl-chloride, bromide, iodide, sulfate, methane sulfonate or paratoluene sulfonate.

The replacement of the halogen atoms X of the intermediate compounds by a

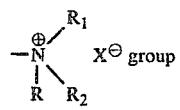

is carried out by reacting said intermediate compound with a tertiary amine having the formula

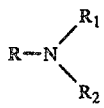

at a temperature of 80°–180° C. at atmospheric pressure or at a higher pressure in an autoclave, without a solvent or in the presence of a solvent for at least one of the reactants which solvent, advantageously, is selected from alcohols, ethers and alkoxy alkanols and preferably ethanol, ethyleneglycol, diethyleneglycol, dipropyleneglycol, the monomethyl- , monoethyl- or monobutylethers or either monoethyleneglycol or diethyleneglycol.

In the formula

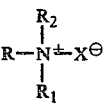

$X^-$ represents $Cl^-$ or $Br^-$ according as epichlorhydrin or epibromhydrin are used as epihalohydrin in the first stage for the preparation of the intermediate oligomer.

The replacement of the halogen atoms of the polyhalogenated intermediate compounds obtained in the first or second stages by

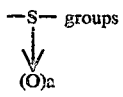

wherein a represents 0 or 1, is carried out by reacting the intermediate compound with a thiol compound such as a mercaptan or an alkaline alkyl mercaptide, preferably, one of sodium or potassium, at a temperature of 80–120° C. at atmospheric pressure or super-atmospheric pressure in an autoclave.

The reaction can be effected without a solvent or in the presence of a solvent for at least one of the reactants and preferably in the presence of a solvent indicated above for the reaction of the polyhalogenated intermediate compounds with a secondary amine.

The useful thiol compounds are, preferably butyl, hexyl, octyl, decyl, dodecyl, tetradecyl, hexadecyl or octadecyl mercaptans, or their alkaline salts.

The polythioether compounds thus obtained can be transformed into polysulfoxides by oxidation with an appropriate oxidizing agent, preferably, with H₂O₂ at a concentration of about 39 weight percent (130 volumes), in the presence of a small amount of an acid, such as acetic acid, at a temperature of 30–50° C., or with a peracid such as performic or peracetic acid.

The present invention also relates to the intermediate compounds of formulas (III) and (IV), below:

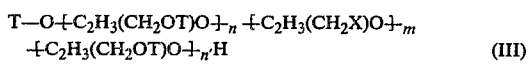

$$T-O+C_2H_3(CH_2OT)O+_n +C_2H_3(CH_2X)O+_m$$
$$+C_2H_3(CH_2OT)O+_{n'}H \qquad (III)$$

and

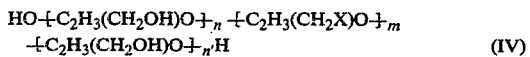

$$HO+C_2H_3(CH_2OH)O+_n +C_2H_3(CH_2X)O+_m$$
$$+C_2H_3(CH_2OH)O+_{n'}H \qquad (IV)$$

wherein T, X, n, m and n' have the meanings given above; $+C_2H_3(CH_2OT)O+$ represents the two isomeric units:

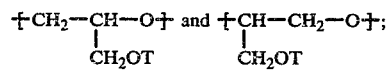

$$+CH_2-CH-O+ \text{ and } +CH-CH_2-O+;$$
$$\quad\quad\quad |\quad\quad\quad\quad\quad\quad\quad |$$
$$\quad\quad CH_2OT\quad\quad\quad\quad\quad CH_2OT$$

and $+C_2H_3(CH_2X)O+$ represents the two isomeric units:

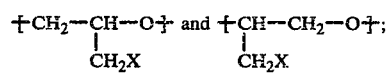

$$+CH_2-CH-O+ \text{ and } +CH-CH_2-O+;$$
$$\quad\quad\quad |\quad\quad\quad\quad\quad\quad\quad |$$
$$\quad\quad CH_2X\quad\quad\quad\quad\quad\quad CH_2X$$

these isomeric units being obtained as a result of the two possible ways in which the oxirane group opens.

The polyhydroxylated sequenced oligomers of formula (I) have good surface activity and their amphipatic characteristics (lipophilic and hydrophilic) can be modified at will be varying the —ZR group and the degrees of polymerization, m, n and n'. They are soluble or dispersible in water depending upon the value of the ratio, $$\frac{n + n'}{m}$$

and the meaning of the —ZR group.

For the same —ZR group, the compounds are all the more hydrophilic as the ratio $$\frac{n + n'}{m}$$

is large.

For the same value of $$\frac{n + n'}{m},$$

the hydrophilic character increases when the number of carbon atoms in R is reduced.

The oligomers include in their sequence, hydroxyl, amine or thioether groups which are reactive sites on which it is possible to effect such various chemical reactions as condensation, telomerization or alkylation reactions.

The oligomers can be used as surfactants, principally as weak foaming agents, wetting agents, detergents, emulsifying agents, peptizing agents, dispersants, softening agents, anticlogging agents, solubilization agents, penetrating agents, anti-redeposition agents, flotation agents, as antistatic finishes or as dyeing aids.

Their molecular weight is between about 500 and 5,000.

Their molecular weight and their weak aggressiveness make the compounds of formula (I) particularly interesting as additives in cosmetic compositions or as excipients in pharmaceutical compositions.

The present invention also relates to pharmaceutical compositions including as an excipient at least one polyhydroxylated sequenced oligomer surfactant of formula (I).

The present invention also relates to cosmetic compositions containing at least one compound of formula (I).

The cosmetic compositions include, principally, composition for use in the care of the skin, nails and hair.

The compositions for the care of the hair are principally washing compositions, especially shampoo compositions, hair conditioning compositions and hair dye compositions.

The hair dye compositions also include one or more dyes, principally oxidation dyes, with or without couplers. They can also include an oxidizing agent, preferably $H_2O_2$. They can further include leucoderivatives of indamines, indoanilines and indophenols, as well as direct dyes, principally azo dyes, anthraquinone dyes, nitrobenzene dyes, indamines, indoanilines or indophenols.

The shampoo compositions can include in addition to the sequenced oligomers surfactant of the present invention, one or more anionic, cationic, amphoteric or nonionic surfactants, as well as other cosmetic adjuvants.

The cosmetic compositions are provided in the form of an aqueous or hydroalcoholic solution or in the form of a cream, a gel, an emulsion or an aerosol.

The hydroalcoholic solution generally includes an alcohol having 1-4 carbon atoms, preferably, ethanol or isopropanol, in an amount ranging from 5 to 70 weight percent based on the total weight of the composition.

The cosmetic and pharmaceutical compositions can include the compounds of formula (I) in an amount ranging from 0.1 to 80 weight percent, advantageously from 0.5 to 40 weight percent, and preferably from 1 to 15 weight percent, based on the total weight of the composition.

The compounds of formula (I) can be used in these compositions as the sole surfactant or in admixture with other anionic, cationic, nonionic or amphoteric type surfactants.

The compositions can also include acids, bases, foam synergists, foam stabilizers, thickening agents, opacifiers, sequesterants, superfatting agents, antiseptics, preservatives, treating products, polymers, pigments, perfumes, dyes, dye solvents, solar filters, oxidizing agents and all other adjuvants conventionally employed in cosmetic compositions which are capillary compositions.

Representative useful acids include hydrochloric, phosphoric, succinic, formic, acetic, lactic, tartaric and citric acids and acid salts such as sodium or potassium acid phosphate.

Representative bases include ammonia, alkaline salts such as neutral sodium or potassium phosphate or sodium or potassium carbonate, or amines such as alkanolamines, for instance, the mono-, di- or tri-ethanol amines, 2-amino-2-methyl propane-1-ol or 2-amino-2-methyl propane 1,3-diol.

The acids and bases are employed in amounts effective to adjust the pH of the compositions to between 3 and 12, and preferably, between 4 and 10.

Representative thickening agents include, principally, cellulosic derivatives such as carboxymethyl cellulose, hydroxypropyl cellulose, hydroxyethyl cellulose and acrylic polymers. The thickening agents are generally employed in an amount of 0.5-20 weight percent based on the total weight of the composition.

Representative opacifiers include, principally, ethyleneglycol monostearate, diglycol stearate, fatty acid alkanolamides, principally lauric, palmitic and stearic alkanolamides and the alkanolamides of copra fatty acids. The opacifiers are generally employed in an amount of 1-10, and preferably 1-2, percent by weight based on the total weight of the composition.

Representative polymers include various cationic, anionic and nonionic polymers generally employed in cosmetic compositions, such as the polymers and copolymers of vinyl pyrrolidone or ethylene imine. These polymers are generally employed in an amount of 1 to 3 percent by weight based on the total weight of the composition.

Representative solvents include principally the glycols such as ethyleneglycol, propyleneglycol, butylglycol, diethyleneglycol and the monomethyl ether of diethyleneglycol. The glycols are employed generally in an amount between 0.5-10, and preferably from 1-6, percent by weight based on the total weight of the composition.

The following non-limiting examples are given to illustrate the invention. Unless otherwise specified all parts and percentages are by weight.

EXAMPLES OF PREPARING THE SEQUENCED OLIGOMER SURFACTANTS

Example IA — Preparation of a Mixture of Polyhydroxylated Polyhalogenated Bisequenced Oligomers of the Formula:

$$H-O+C_2H_3(CH_2OH)O+_{10} +C_2H_3(CH_2Cl))O+_5H$$

To 14.8 g of tertiobutyl alcohol (0.2 mole), there are added over a 2½ hour period, at a temperature of 70° C., alternately in 3 fractions, 0.69 ml of $BF_3$ etherate and 260 g (2 moles) of tertiobutyl glycidyl ether.

The temperature and agitation of the resulting mixture are maintained for 2 hours and 45 minutes. One checks by dosage that all the epoxide has been consumed. There are then added, alternately in 3 fractions at 70° C., 0.9 ml of $BF_3$ etherate and 92.5 g (1 mole) of epichlorohydrin. The addition lasts for 50 minutes.

After 1½ hours of agitation at 70° C., the reaction is practically complete. The hydroxyl index of the product obtained is 1.10 meg/g.

The product is washed three times, each time with 500 ml of boiling water. The washed product is then dehydrated by heating under reduced pressure.

After removing the most volatile materials (15.6%) by molecular distillation at a temperature of 180° C., there is obtained a product having a molecular weight of 1,730, whose hydroxyl index is 0.94 meq/g and whose chlorine index is 2.59 meq/g.

This product is in the form of a pale yellow oil.

To the polyhalogenated polytertiobutyl derivative thus obtained, there are added 3 grams of sulfoacetic acid. The resulting mixture is then heated for 3½ hours at 95° C.

There are then slowly added 30 ml of water and the heating is continued for an additional 1 hour.

The reaction mixture is then diluted with water to a concentration of 10%. The catalyst is removed by passing the diluted reaction mixture over Amberlite MB I resin; the water is then removed by evaporation under reduced pressure.

There is thus obtained a deep brown polyhydroxylated polyhalogenated derivative whose hydroxyl index is 11.5 meq/g and whose chlorine index is 3.2 meq/g.

Example IB — Preparation of a Mixture of Polyhydroxylated Polysulfoxide Nonionic Bisequenced Oiligomers of the Formula:

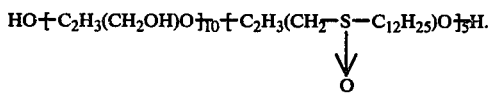

To 15 g (56 meq) of the polyhydroxylated polyhalogenated derivative prepared in Example IA, there are added 11.5 g (56 meq) of lauryl mercaptan and 20 ml of absolute ethanol. The resulting mixture is heated to 70° C. There are then slowly added, with agitation and under a nitrogen atmosphere, 9 g of sodium methylate (6.2 meq/g) and the mixture is heated at reflux for 4 hours. The reaction mixture is then diluted with 70 ml of absolute ethanol and the sodium chloride formed in filtered.

After removal of the solvent under reduced pressure there is obtained an amber colored soft paste.

To 20 g (40 meq) of the mixture of thioethers thus prepared, there is initially added, with strong agitation 0.5 ml of acetic acid, and then at 35° C. there are slowly added 3.44 ml (40 meq) of $H_2O_2$ (130 volumes).

There is thus obtained a soft paste which is dispersible in water.

Example IC — Preparation of a Mixture of Polyhydroxylated Cationic Bisequenced Oligomers of the Formula:

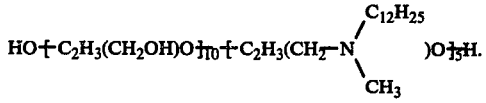

To 22 g of the mixture of polyhydroxylated polychlorinated derivatives prepared in Example IA, there are added 34 g (168 meq) of methyl laurylamine. The resulting mixture is heated with agitation and under a nitrogen atmosphere at 130° C. for 6 hours.

The amount of transformation of the chloride is close to 100%. The reaction mixture is then diluted with 100 ml of isopropanol and the acid formed is neutralized with 7.8 g of sodium hydroxide (9.9 meq/g). The sodium chloride formed is filtered and the solvent is distilled under reduced pressure. The excess methyl laurylamine is then removed by molecular distillation at 140° C., yielding a black brown pastey product.

After dissolution of this product in water, there is a slight opalescence which disappears by the addition thereto of a small amount of a mineral or organic acid.

Example IIA — Preparation of a Mixture of Polytertiobutoxy Polyhalogenated Bisequenced Oligomers of the Formula:

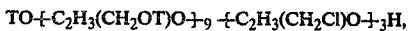

wherein T represents tertiobutoxy.

To 14.8 g (200 meq) of tertiobutyl alcohol, there are added, with agitation, at 70° C. and in three equal fractions, 0.61 ml of BF₃ etherate and 234 g (1800 meq) of tertiobutyl glycidyl ether. The addition lasts 1½ hours.

To the product thus obtained, having a hydroxyl index of 1.20 meq/g, there are added at 80° C., 0.14 ml of BF₃ etherate and 55.5 g (600 meq) of epichlorohydrin over a 30 minute period. The temperature and agitation of this mixture is maintained for 2 hours.

At that point the epoxide is practically all consumed. The product is washed three times, each time with 50 ml of boiling water. The washed product is then dehydrated by heating under reduced pressure. After removing the volatile materials by molecular distillation at 160° C., there is obtained a pale yellow viscous liquid having a molecular weight of 1,060 and an organic chlorine content of 1.87 meq/g.

Example IIB — Preparation of a Mixture of Polyhydroxylated Polysulfoxide Nonionic Bisequenced Oligomers of the Formula:

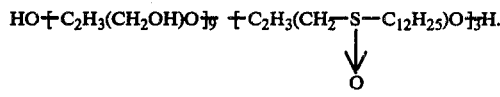

To 40 g (74.8 meq) of the polyhalogenated derivative prepared in Example IIA, there are added 15.6 g (74.8 meq) of lauryl mercaptan. To the resulting mixture, under a nitrogen atmosphere, at 65° C., there are slowly added 12.1 g of sodium methylate (6.2 meq/g).

This mixture is then heated for 5 hours at about 80° C. The rate of reaction, determined by dosage of the alkalinity and remaining mercaptans, is 91.5%. The resulting product is washed three times with 100 ml of boiling water. The water is then removed by heating under reduced pressure.

The tertiobutoxy groups are then hydrolyzed by heat at 95° C. for 3 hours in the presence of 0.4 g of sulfoacetic acid. There are then slowly added 5 ml of water and the mixture is continued to be heated for 1 more hour. The resulting product is a brown viscous oil which is dispersible in water. Its hydroxyl index is 4.7 meq/g and its sulfur content in the form of thioether is 1.5 meq/g.

To 25 g of this derivative there is initially added 0.15 ml of acetic acid. Then, at 35° C. there are slowly added 3.2 ml of H₂O₂ (130 volumes), yielding an amber colored, very thick oil which is soluble in water.

Example IIC — This Example Illustrates a Variation of the Process Described in Example IIB To 100 g of the polyhalogenated derivative prepared in Example IIA, there is added 1 g of sulfoacetic acid. This mixture is heated at 90° C. for 1½ hours. Ther are then slowly added 5 ml of water and heating is continued for an additional 1½ hours.

To 28.5 g (83 meq-Cl) of the immediately preceding derivative (Hydroxyl Index - 11.5 meq/g) there are added 17.5 g (83 meq) of lauryl mercaptan and 15 ml of absolute ethanol. This mixture is heated to 60° C. and there are added thereto under a nitrogen atmosphere 13.4 g of sodium methylate (6.2 meq/g).

This mixture is maintained at reflux temperature for 5 hours. The reaction rate, determined by dosage of the alkalinity and remaining mercaptans is 93-95%.

There are then added to the reaction mixture 100 ml of absolute ethanol. The sodium chloride which was formed is filtered and then the alcohol is removed by heating under reduced pressure.

To 30 g (62 meq) of the resulting polythioether, there is initially added 0.15 ml of acetic acid. Then at 35° C. under strong agitation there are slowly added 5.36 ml of H₂O₂ (130 volumes).

The product thus obtained is a light chestnut colored soft paste which is soluble in water.

Example IID — Preparation of a Mixture of Polyhydroxylated Cationic Bisequenced Oligomers of the Formula:

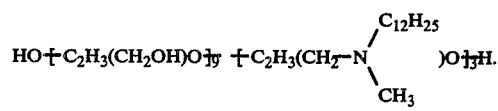

To 35 g (102 meq-Cl) of the polyhalogenated derivative prepared in Example IIA, there are added 24 g (214 meq) of methyl laurylamine. The resulting mixture is heated under a nitrogen atmosphere for 5 hours at 130° C.

This reaction mixture is dissolved in 100 ml of isopropanol and there are added thereto 9.75 g of sodium hydroxide (9.9 meq/g).

The sodium chloride formed is separated by filtration and the excess methyl laurylamine is removed under reduced pressure. There is thus obtained a deep brown colored soft paste which produces cloudiness when admixed with water. However, on the addition of a mineral or organic acid thereto the solution becomes perfectly clear.

Example IIE — Prepartion of a Mixture of Polyquaternary Polyhydroxylated Bisequenced Oligomer of the Formula:

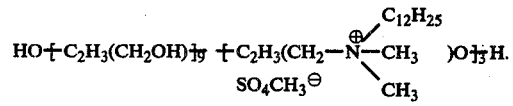

To 16 g (29 meq of basicity) of the mixture of compounds obtained in Example IID, there are slowly added 3.6 g of dimethyl sulfate at a temperature of 50° C. The reaction is exothermic and the temperature is maintained using a cooling bath. The addition lasts 1 hour.

There is thus obtained a light brown paste which is soluble in water. The rate of quaternization is 90%.

Example IIIA — Preparation of a Mixture of Polyhalogenated Trisequenced Oligomers of the Formula:

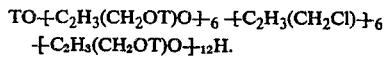

To 4.5 g (0.06 mole) of tertiobutyl alcohol there is initially added 0.2 ml of the acetic acid complex of boron trifluoride, and then at 80° C., over a 1 hour period, there are added 46.5 g (0.36 mole) of tertiobutyl glycidyl ether. After 1 hour of agitation, there is initially added 0.2 ml of BF₃ and then over a 1½ hour period 33 g (0.36 mole) of epichlorohydrin. After complete consumption of the epichlorohydrin there are again added 0.4 ml of BF₃ and 93.5 g (0.72 mole) of tertiobutyl glycidyl ether over a 2 hour period.

The resulting product is washed three times with 400 ml of boiling water. It is then dehydrated under reduced pressure.

After removal, by molecular distillation of the volatile materials, there is obtained a light yellow viscous product having a molecular weight of 1,000 and an organic chlorine index of 2.17 meq/g.

Example IIIB — Preparation of a Mixture of Polyhydroxylated Polysulfoxide Nonionic Trisequenced Oligomers of the Formula:

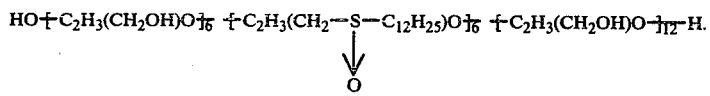

To 90 g (195 meq-Cl) of the polyhalogenated derivative prepared in Example IIIA, there is added 0.8 g of sulfoacetic acid. This mixture is heated for 1 hour and 15 minutes at about 95° C. There are then slowly added 5 ml of water and the heating is continued for an additional 3 hours.

The resulting product is then dissolved in 50 ml of water and 75 ml of isopropanol. The acidity is neutralized by stirring this mixture with 13 g of Amberlite MB 1 resin.

The resin is then filtered and the solvents are removed by heating under reduced pressure. The product thus obtained is a brown colored, sticky, very soft paste, which produces slight cloudiness when added to water.

To 22 g (73.3 meq) of the immediately preceding derivative, there are initially added 12 ml of ethanol, and then 15.4 g (73.3 meq) of lauryl mercaptan. The resulting mixture is heated to 65° C. and there are slowly added thereto 11.8 g of sodium methylate (6.2 meq/g). The reaction mixture is maintained at reflux temperature of the alcohol for 5½ hours. The rate of reaction is 93%.

After filtering the sodium chloride, there is obtained a product in the form of a brown colored, sticky, very soft paste which is dispersible in water.

To 24 g of the immediately preceding derivative (52.5 meq-sulfur in the form of thioether) there is initially added 0.12 ml of acetic acid, and then at 35° C., with strong agitation, there are added 4.52 ml of H₂O₂ (130 volumes) of about 39% w/w over a 25 minute period. The product obtained is in the form of an amber colored soft paste which is soluble in water.

Example IVA — Preparation of a Mixture of Polyhydroxylated Polyhalogenated Bisequenced Oligomers of the Formula:

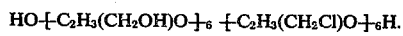

To 14.8 g (0.2 mole) of tertiobutyl alcohol, there are added at a temperature of 70°–75° C., 0.43 ml of BF₃ etherate, 3 times, and 156 g (1.2 moles) of tertiobutyl glycidyl ether in a period of 1 hour and 15 minutes. The resulting mixture is left to stand, with agitation for 1 hour at 75° C.

To the resulting product there are added at 70°–75° C., 0.55 ml of BF₃ etherate, 3 times, and 111 g (1.2 moles) of epichlorohydrin. The addition lasts for 1 hour. The reaction mixture is then agitated at 80° C. for an additional 2 hours.

After complete disapperance of the epoxide groups, the product is washed three times with 300 ml of boiling water. It is then dehydrated by heating under reduced pressure and subsequently topped by molecular distillation at 175° C. The resulting product is an amber colored very viscous liquid.

Analysis: Cl:4.32–4.36 meq/g; Hydroxyl Index: 1.42–1.40 meq/g; M.W. = 830.

To 50 g of the immediately preceding derivative there is added 0.5 g of sulfoacetic acid. The resulting mixture is heated at 90° C. for 1 hour. There are then added 2 ml of water and the heating and agitation are continued at 100° C. for 1 hour.

After dehydration by heating at 105° C. under reduced pressure, there is obtained a deep colored thick product whose hydroxyl index is 7.84–7.94 meq/g.

Example IVB—Preparation of a Mixture of Cationic Bisequenced Oligomers of the Formula:

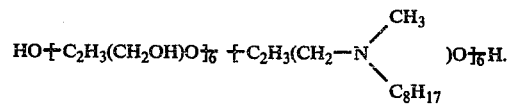

To 37 g (216 meq-Cl) of the polyhydroxylated polyhalogenated derivative prepared in Example IVA, there are added 33 g of methyl octylamine. This mixture is then heated at 130° C. for 4 hours. The acid formed is neutralized with 21.5 g of 10 N NaOH.

The product is then washed three times with 100 ml of boiling water in the presence of 20 ml of primary butanol. The resulting product is a very thick oil which is soluble in acidified water.

EXAMPLES OF USE

Example A1

A hair dye composition containing oxidation dyes is prepared by admixing the following components:

| Carrier or Vehicle | |
|---|---|
| Compound prepared in Example IIB | 4 g |
| Cetyl stearyl alcohol | 18 g |
| Sodium cetyl stearyl sulfate | 6 g |

-continued

|  |  |
|---|---|
| Triethanolamine lauryl sulfate, 40% active material | 5 g |
| Ammonia, 22° Bé | 12 ml |
| Dyes |  |
| Meta diamino anisol sulfate | 0.048 g |
| Resorcinol | 0.0420 |
| Meta amino phenol base | 0.150 g |
| Nitro-p-phenylenediamine | 0.085 g |
| Paratoluylenediamine | 0.004 g |
| Ethylenediamine tetra acetic acid | 1 g |
| Sodium bisulfite, d = 1.32 | 1.200 g |
| Water, sufficient for | 100 g |

30 g of the cream resulting from this admixture are mixed in a bowl with 45 g of $H_2O_2$ (20 volumes). There is thus obtained a smooth consistent cream which is pleasant to apply and which adheres well to the hair.

This cream is then applied to the hair with a brush and is permitted to remain in contact therewith for 30 minutes. Thereafter, the hair is rinsed. The thus treated hair combs easily and is silky to the touch. The hair is then set and dried. The hair thus treated is shiny and lively; is silky to the touch; and combs easily. On 100% white hair a blonde coloration is obtained.

Example A2

A hair dye composition, containing oxidation dyes, is prepared by admixing the following components:

|  |  |
|---|---|
| Carrier or Vehicle |  |
| Compound of Example IIIB | 3 g |
| Cetyl alcohol | 20 g |
| Sodium cetyl stearyl sulfate | 5 g |
| Ammonium lauryl sulfate, 20% fatty alcohol | 10 g |
| Ammonia, 22° Bé | 11 ml |
| Dyes |  |
| Meta diamino anisol sulfate | 0.048 g |
| Resorcinol | 0.0420 g |
| Meta amino phenol base | 0.150 g |
| Nitro-p-phenylenediamine | 0.085 g |
| Paratoluylenediamine | 0.004 g |
| Ethylenediamine tetra acetic acid | 1 g |
| Sodium bisulfite, d = 1.32 | 1.200 g |
| Water, q.s.p. | 100 g |

30 g of the cream resulting from this admixture are mixed in a bowl with 45 g of $H_2O_2$ (20 volumes). There is thus obtained a smooth, consistent cream which is pleasant to apply and which adheres well to the hair.

This cream is then applied to the hair with a brush and is permitted to remain in contact therewith for 30 minutes. Thereafter, the hair is rinsed. The thus-treated hair combs easily and is silky to the touch. The hair is then set and dried. The dried hair is shiny and lively; is silky to the touch; and it combs easily. On 100% white hair a blonde coloration is obtained.

Example A3

A hair dye composition, containing oxidation dyes, is prepared by admixing the following components:

|  |  |
|---|---|
| Carrier or Vehicle |  |
| Compound of Example IC | 4 g |
| Cetyl stearyl alcohol | 20 g |
| Sodium cetyl stearyl sulfate | 4 g |
| Ammonium lauryl sulfate, 20% fatty alcohol | 12 g |
| Ammonia, 22° Bé | 11 ml |
| Dyes |  |
| Meta diamino anisol sulfate | 0.048 g |
| Resorcinol | 0.0420 g |
| Meta amino phenol base | 0.150 g |
| Nitro-p-phenylenediamine | 0.085 g |
| Paratoluylenediamine | 0.004 g |
| Ethylenediamine tetra acetic acid | 1 g |
| Sodium bisulfite, d = 1.32 | 1.200 g |
| Water, sufficient for | 100 g |

30 g of the cream resulting from this admixture are mixed in a bowl with 45 g of $H_2O_2$ (20 volumes). There is thus obtained a smooth, consistent cream which is pleasant to apply and which adheres well to the hair.

This cream is then applied to the hair with a brush and is permitted to remain in contact therewith for 30 minutes. The hair is then rinsed and the thus-treated hair combs easily and is silky to the touch. The hair is then set and dried. The dry hair is shiny and lively; it is silky to the touch; and it combs easily. On 100% white hair a blonde coloration is obtained.

Example A4

A hair dye composition, containing oxidation dyes, is prepared by admixing the following components:

|  |  |
|---|---|
| Carrier or Vehicle |  |
| Compound of Example IIE | 5 g |
| Cetyl stearyl alcohol | 15 g |
| Sodium cetyl stearyl sulfate | 6 g |
| Monoethanolamine lauryl sulfate, 20% fatty alcohol | 10 g |
| Ammonia, 22° Bé | 12 g |
| Dyes |  |
| Meta diamino anisol sulfate | 0.048 g |
| Resorcinol | 0.0420 g |
| Meta amino phenol base | 0.150 g |
| Nitro-p-phenylenediamine | 0.085 g |
| Paratoluylenediamine | 0.004 g |
| Ethylenediamine tetra acetic acid | 1 g |
| Sodium bisulfite, d = 1.32 | 1.200 g |
| Water, sufficient for | 100 g |

30 g of the cream resulting from this admixture are mixed in a bowl with 45 g of $H_2O_2$ (20 volumes). There is thus obtained a smooth, consistent cream which is pleasant to apply and which adheres well to the hair.

This cream is then applied to the hair with a brush and is permitted to remain in contact therewith for 30 minutes. The hair is then rinsed and the thus-treated hair combs easily and is silky to the touch. The hair is then set and dried. The dry hair is shiny and lively; it is silky to the touch; and it combs easily. On 100% white hair a blonde coloration is obtained.

What is claimed is:

1. A polyhydroxylated sequenced oligomer surfactant comprising a compound or a mixture of compounds having the formula:

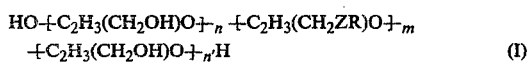

wherein
R is linear alkyl having 4–18 carbons atoms;
Z is selected from

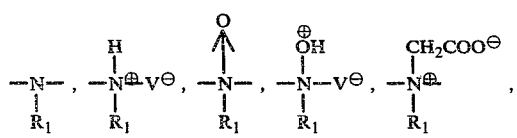

-continued $$\overset{R_2}{\underset{R_1}{\overset{|}{\oplus N}}}-Y^{\ominus}, \text{ or } -\overset{|}{\underset{(O)_a}{S}}-$$

wherein $R_1$ and $R_2$ each independently represent methyl, ethyl or hydroxyethyl, Y represents an anion selected from chloride, bromide, iodide, methyl sulfate, methane sulfonate or paratoluene sulfonate, $HR_1N^{\oplus}V^{\ominus}$ and $R_1NO^{\oplus}H.V^{\ominus}$ represents a mineral acid or an organic acid salt of an amine or an amine oxide selected from the hydrochloride, hydrobromide, sulfate, phosphate, acetate, lactate, tartrate, oxalate or succinate thereof, and a represents 0 or 1;

$+C_2H_3(CH_2OH)O+$ represents the two isomers:

$$+CH_2-\underset{CH_2OH}{\overset{|}{CH}}-O+ \text{ and } +\underset{CH_2OH}{\overset{|}{CH}}-CH_2-O+ ;$$

$+C_2H_3(CH_2ZR)O+$ represents the two isomers:

$$+CH_2-\underset{CH_2-Z-R}{\overset{|}{CH}}-O+ \text{ and } +\underset{CH_2-Z-R}{\overset{|}{CH}}-CH_2-O+;$$

m represents a whole or decimal number from 2 to 10;
n represents a whole or decimal number from 2 to 25;
n' represents 0 or a whole or decimal number from 2 to 25; and
n + n' represents a whole or decimal number from 2 to 25.

2. The surfactant of claim 1 wherein Z is $$-\underset{R_1}{\overset{|}{N}}-,$$

R is $-C_{12}H_{25}$; $R_1$ is $-CH_3$; n = 10; N' is 0 and m = 5.

3. A polyhydroxylated bisequenced oligomer surfactant having the formula $$HO+C_2H_3(CH_2OH)O\overline{]_n}[C_2H_3(CH_2ZR)O\overline{]_m}H$$

wherein
R is linear alkyl having 4-18 carbon atoms;
Z is $$-\underset{R_1}{\overset{|}{N}}-,$$

wherein $R_1$ and $R_2$ each independently represent methyl, ethyl or hydroxy ethyl;
$+C_2H_3(CH_2OH)O+$ represents the two isomers:

$$+CH_2-\underset{CH_2OH}{\overset{|}{CH}}-O+ \text{ and } +\underset{CH_2OH}{\overset{|}{CH}}-CH_2-O+;$$

$+C_2H_3(CH_2ZR)O+$ represents the two isomers:

$$+CH_2-\underset{CH_2-Z-R}{\overset{|}{CH}}-O+ \text{ and } +\underset{CH_2-Z-R}{\overset{|}{CH}}-CH_2-O+;$$

m represents a whole or decimal number from 2 to 10; and
n represents a whole or decimal number from 2 to 25.

4. A polyhydroxylated trisequenced oligomer surfactant having the formula $$HO+C_2H_3(CH_2OH)O\overline{]_n}[C_2H_3(CH_2Z-R)O\overline{]_m}[C_2H_3(CH_2OH)O\overline{]_{n'}}H$$

wherein
R is linear alkyl having 4-18 carbon atoms;
Z is $$-\underset{R_1}{\overset{|}{N}}-$$

wherein $R_1$ and $R_2$ each independently represent methyl, ethyl or hydroxy ethyl;
$+C_2H_3(CH_2OH)O+$ represents the two isomers:

$$+CH_2-\underset{CH_2OH}{\overset{|}{CH}}-O+ \text{ and } +\underset{CH_2OH}{\overset{|}{CH}}-CH_2-O+;$$

$+C_2H_3(CH_2ZR)O+$ represents the two isomers:

$$+CH_2-\underset{CH_2-Z-R}{\overset{|}{CH}}-O+ \text{ and } +\underset{CH_2-Z-R}{\overset{|}{CH}}-CH_2-O+;$$

m represents a whole or decimal number from 2 to 10;
n represents a whole or decimal number from 2 to 25;
n' represents a whole or decimal number from 2 to 25; and
n + n' represents a whole or decimal number from 2 to 25.

5. The surfactant of claim 1, wherein n' is 0; Z is $$-\underset{O(a)}{\overset{|}{S}}-;$$

a is 1; R is $-C_{12}H_{25}$; n is 10; and m is 5.

6. The surfactant of claim 1, wherein n' is 0; Z is $$-\underset{O(a)}{\overset{|}{S}}-;$$

a is 1; R is $-C_{12}H_{25}$; m is 3; and n is 9.

7. The surfactant of claim 1, wherein n' is 0; m is 3; Z is $$-\underset{R_1}{\overset{|}{N}}-,$$

$R_1$ being methyl; R is $-C_{12}H_{25}$; and n is 9.

8. The surfactant of claim 1, wherein n' is 0; m is 3; R is $-C_{12}H_{25}$; Z is

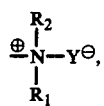
$R_1$ and $R_2$ being methyl; Y is methyl sulfate; and n is 9.
9. The surfactant of claim 1, wherein n' is 12; m is 6; n is 6; Z is
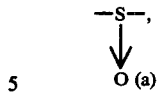
a being 1; and R is $-C_{12}H_{25}$.
10. The surfactant of claim 1, wherein n' is 0; m is 6; n is 6; Z is
$R_1$ being methyl; and R is $-C_8H_{17}$.
* * * * *